United States Patent [19]

Chodnekar et al.

[11] 4,256,748
[45] Mar. 17, 1981

[54] IMIDAZO[2,1-b]QUINAZOLIN-2(3H)-ONES AND PHARMACEUTICAL COMPOSITIONS FOR TREATMENT AND PROPHYLAXIS OF CARDIAC INSUFFICIENCY AND CARDIAC FAILURE

[75] Inventors: Madhukar S. Chodnekar, Seltisberg; Ado Kaiser, Lausen, both of Switzerland

[73] Assignee: Hoffmann-La Roche Inc., Nutley, N.J.

[21] Appl. No.: 50,395

[22] Filed: Jun. 20, 1979

Related U.S. Application Data

[63] Continuation-in-part of Ser. No. 924,117, Jul. 13, 1978, abandoned.

[30] Foreign Application Priority Data

Jul. 25, 1977 [LU] Luxembourg ............... 77829
May 26, 1978 [CH] Switzerland ............... 5776/78

[51] Int. Cl.³ .................. A61K 31/505; C07D 487/04
[52] U.S. Cl. ........................ 424/251; 544/250; 544/283; 544/286; 544/291; 560/36; 560/37; 548/311; 564/384
[58] Field of Search ............... 424/251; 544/250

[56] References Cited

U.S. PATENT DOCUMENTS

| | | |
|---|---|---|
| 3,932,407 | 1/1976 | Beverung, Jr. et al. ............ 544/250 |
| 3,983,119 | 9/1976 | Beverung, Jr. et al. ............ 544/250 |
| 3,988,340 | 10/1976 | Partyka et al. ............ 544/250 |

FOREIGN PATENT DOCUMENTS

| | | |
|---|---|---|
| 2305575 | 8/1973 | Fed. Rep. of Germany . |
| 64/3710 | 2/1965 | South Africa . |
| 1037375 | 7/1966 | United Kingdom . |
| 1067745 | 5/1967 | United Kingdom . |
| 1418822 | 12/1975 | United Kingdom . |
| 2001638 | 2/1979 | United Kingdom . |

OTHER PUBLICATIONS

Jen et al., J. Med. Chem., vol. 15, No. 7, pp. 727–731 (1972).
Loev et al., Experientia, p. 875, (08/15/71).

*Primary Examiner*—Donald G. Daus
*Assistant Examiner*—Diana G. Rivers
*Attorney, Agent, or Firm*—Jon S. Saxe; Bernard S. Leon; William G. Isgro

[57] ABSTRACT

Compounds of the formula

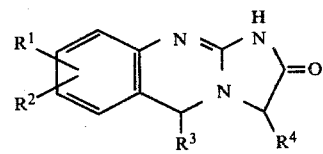

wherein $R^1, R^2, R^3$ and $R^4$ are as hereinafter described, tautomers and salts thereof, are disclosed. The foregoing compounds inhibit the aggregation of blood platelets which renders them useful as therapeutic agents in the prophylaxis of thromboses. Furthermore, they are useful for the treatment and prophylaxis of cardiac insufficiency and cardiac failure, due to their inotropic activity without substantial tachycardia.

11 Claims, No Drawings

IMIDAZO[2,1-b]QUINAZOLIN-2(3H)-ONES AND PHARMACEUTICAL COMPOSITIONS FOR TREATMENT AND PROPHYLAXIS OF CARDIAC INSUFFICIENCY AND CARDIAC FAILURE

CROSS-REFERENCE TO RELATED APPLICATIONS

This application is a continuation-in-part of U.S. patent application Ser. No. 924,117, filed July 13, 1978, now abandoned.

BRIEF SUMMARY OF THE INVENTION

The invention relates to compounds of the formula

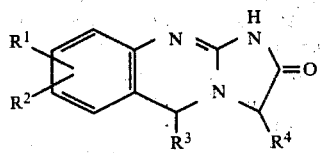

wherein $R^1$ and $R^2$, independently, are hydrogen, halogen, lower alkyl, hydroxy, lower alkoxy, hydroxy-(lower alkyl), (lower alkoxy)-(lower alkyl), phenyl, phenoxy, amino, lower alkylamino or di(-lower alkyl)amino, or $R^1$ and $R^2$ on adjacent carbon atoms taken together are methylenedioxy, $R^3$ is hydrogen, lower alkyl or phenyl, and $R^4$ is lower alkyl, hydroxy-(lower alkyl), (lower alkoxy)-(lower alkyl), aryl-(lower alkyl) or aryl, tautomers thereof and pharmaceutically acceptable acid addition salts thereof.

In another aspect, the invention relates to intermediates of the formula

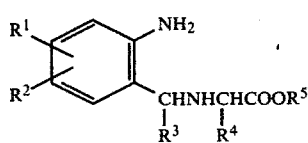

wherein $R^1$, $R^2$, $R^3$ and $R^4$ are as previously described, and $R^5$ is lower alkyl.

DETAILED DESCRIPTION OF THE INVENTION

The imidazoquinazoline derivatives of the invention are compounds of the formula

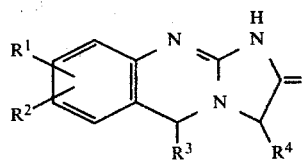

wherein $R^1$ and $R^2$, independently, are hydrogen, halogen, lower alkyl, hydroxy, lower alkoxy, hydroxy-(lower alkyl), (lower alkoxy)-(lower alkyl), phenyl, phenoxy, amino, lower alkylamino or di(lower alkyl)amino, or $R^1$ and $R^2$ on adjacent carbon atoms taken together are methylenedioxy, $R^3$ is hydrogen, lower alkyl or phenyl, and $R^4$ is lower alkyl, hydroxy-(lower alkyl), (lower alkoxy)-(lower alkyl), aryl-(lower alkyl) or aryl, tautomers thereof and pharmaceutically acceptable acid addition salts thereof.

The term "lower" used herein refers in particular to groups containing 1-6, preferably 1-4, carbon atoms. The alkyl groups can be straight-chain or branched-chain. Exemplary of alkyl groups are methyl, ethyl, propyl, isopropyl, butyl, isobutyl, pentyl, hexyl, and the like. The alkoxy groups can be straight-chain or branched-chain. Exemplary of alkoxy groups are methoxy, ethoxy, propoxy, isopropoxy, butoxy, isobutoxy, pentoxy, hexoxy, and the like. The term "aryl" denotes in particular phenyl or phenyl substituted by halogen, lower alkyl, hydroxy and/or lower alkoxy. The term "halogen" denotes chlorine, bromine, fluorine and iodine.

Among the compounds of formula I, those which exist in the D-form are preferred. In addition, compounds of formula I wherein $R^1$ and $R^3$ are hydrogen, $R^2$ is halogen in the 6- or 7-position or lower alkyl in the 6-position, preferably chlorine in the 6-position, bromine in the 7-position or methyl in the 6-position, and $R^4$ is lower alkyl, preferably methyl, are also preferred.

Especially preferred imidazoquinazoline derivatives provided by the invention are:

D-6-chloro-1,5-dihydro-3-methyl-imidazo[2,1-b]quinazolin-2(3H)-one;
D-7-bromo-1,5-dihydro-3,6-dimethyl-imidazo[2,1-b]quinazolin-2(3H)-one, and their salts.

Exemplary of other imidazoquinazoline derivatives provided by the invention are:

D-6-chloro-1,5-dihydro-7-methoxy-3-methyl-imidazo[2,1-b]quinazolin-2-(3H)-one;
D-6,7-dichloro-1,5-dihydro-3-methyl-imidazo[2,1-b]quinazolin-2(3H)-one;
D-7-bromo-6-chloro-1,5-dihydro-3-methyl-imidazo[2,1-b]quinazolin-2(3H)-one;
D-3,6-dimethyl-1,5-dihydro-imidazo[2,1-b]quinazolin-2-(3H)-one;
L-3,6-dimethyl-1,5-dihydro-imidazo[2,1-b]quinazolin-2(3H)-one;
L-3,9-dimethyl-1,5-dihydro-imidazo[2,1-b]quinazolin-2(3H)-one;
D-7-bromo-1,5-dihydro-3-methyl-imidazo[2,1-b]quinazoline-2(3H)-one, and their pharmaceutically acceptable acid addition salts.

The compounds of formula I can exist in various tautomeric forms. The invention is therfore not restricted to compounds of formula I reproduced hereinbefore, but also includes the tautomers, for example, those of the formulas

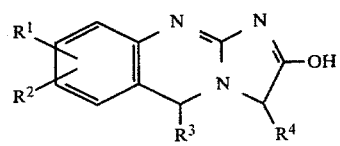

and

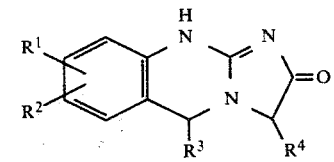

wherein $R^1$, $R^2$, $R^3$ and $R^4$ are as previously described.

The compounds of formula I and their tautomers, for example, of formulas Ia and Ib, can also exist in the form of racemates or as the respective optically active compound. All of these forms form part of the invention.

The compounds of formula I form physiologically compatible salts or pharmaceutically acceptable acid addition salts. Exemplary of such salts are those formed with mineral acid salts such as hydrochlorides, hydrobromides, sulfates, phosphates, or the like, and those formed with organic sulfonic acids, such as alkylsulfates and arylsulfonates, and carboxylic acid salts, such as succinates, citrates, tartrates, maleates, or the like.

According to the process of the invention, the imidazoquinazoline derivatives, that is, the compounds of formula I, tautomers thereof and salts of such compounds, are prepared by (a) reacting a compound of the formula

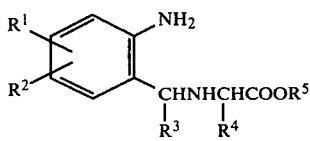

II wherein $R^1$, $R^2$, $R^3$ and $R^4$ are as previously described, and $R^5$ is lower alkyl,
with cyanogen bromide, or
(b) treating a compound of the formula

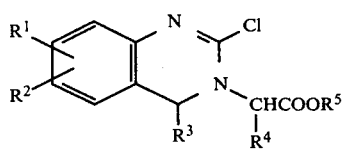

III wherein $R^1$, $R^2$, $R^3$, $R^4$ and $R^5$ are as previously described,
with ammonia, and, if desired, converting a resulting compound of formula I or tautomer thereof into a salt or a pharmaceutically acceptable acid addition salt.

The reaction of a compound of formula II with cyanogen bromide according to process embodiment (a) is conveniently carried out, while warming, in a solvent, for example, a lower alkanol, such as ethanol, or the like.

The treatment of a compound of formula III with ammonia according to process embodiment (b) is conveniently carried out, while warming, in a solvent, for example, a lower alkanol, such as ethanol, or the like, and water.

A compound of formula I, wherein $R^1$ and/or $R^2$ are hydrogen can be halogenated in a known manner. Thus, for example, a solution of a compound of formula I, which is unsubstituted in the 6-, 7-, 8- and 9-positions, in acetic acid can be reacted with bromine to give a 7-bromo compound of formula I.

The compounds of formula I wherein $R^1$ and $R^2$ are other than an amino, lower alkylamino or di(lower alkyl)amino can be prepared according to Formula Scheme I hereinafter, wherein Y is chlorine or bromine, $R^{11}$ and $R^{21}$ have any of the values accorded to $R^1$ and $R^2$ hereinbefore with the exception of amino, lower alkylamino and di(lower alkyl)amino and $R^3$ and $R^4$ are as hereinbefore described.

Further, the compounds of formula I can be prepared according to Formula Scheme II hereinafter, wherein Z is oxygen or sulfur, M is ammonium, potassium or sodium and $R^1$, $R^2$, $R^3$ and $R^4$ are as hereinbefore described.

FORMULA SCHEME I

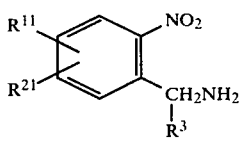

Hydrogen/platinum, palladium or Raney Nickel
for example, in ethanol

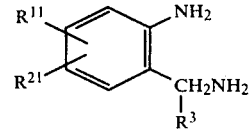

Cyanogen bromide, for example, in ethanol

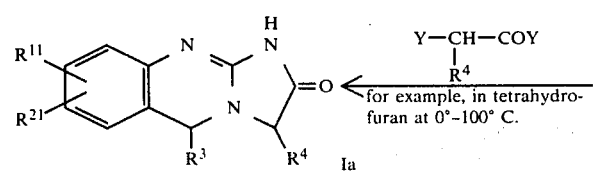

Y—CH—COY
|
$R^4$
for example, in tetrahydrofuran at 0°–100° C.

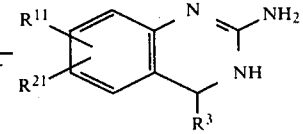

Ia

FORMULA SCHEME II

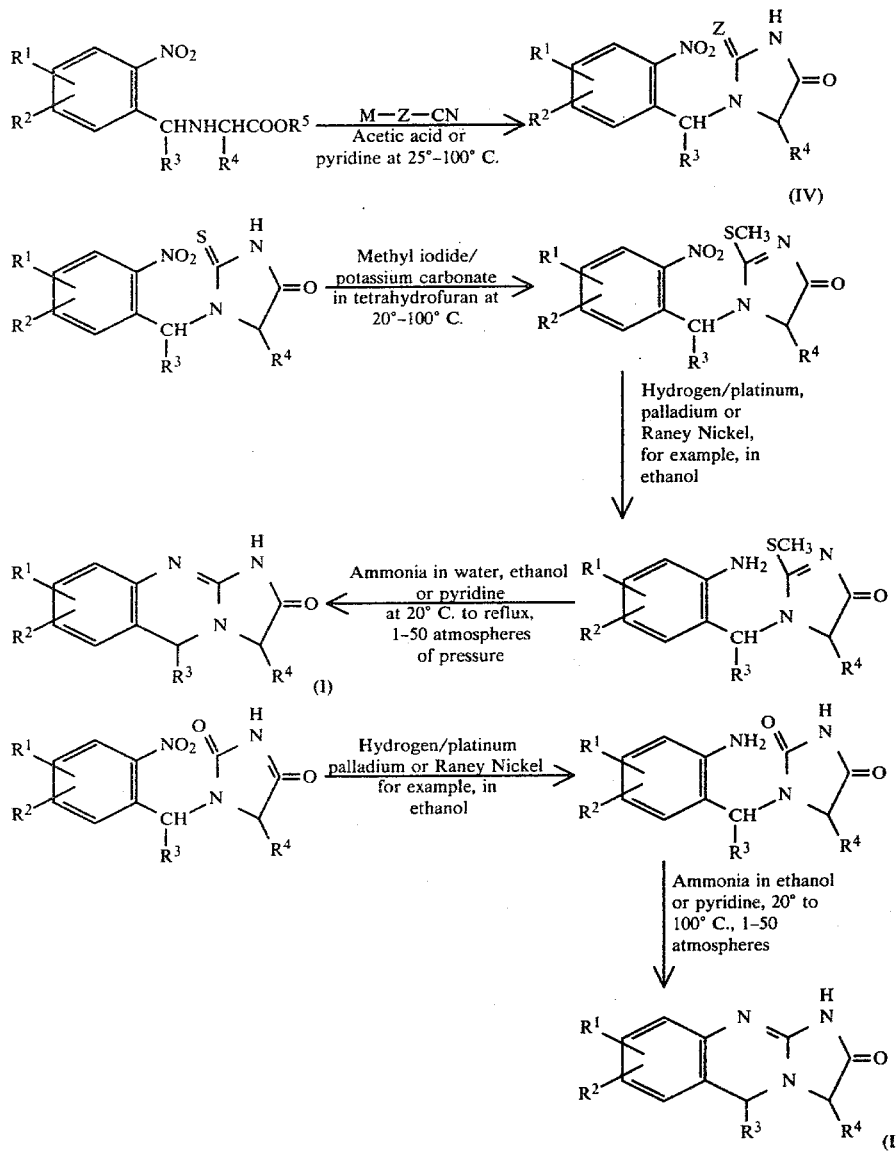

The starting materials of formula II also form part of this invention.

The starting materials of formulas II and III can be prepared according to Formula Scheme III hereinafter, wherein X is halogen and $R^1$, $R^2$, $R^3$, $R^4$ and $R^5$ are as described hereinbefore, or in an analogous manner to the methods set forth in the Examples.

FORMULA SCHEME III

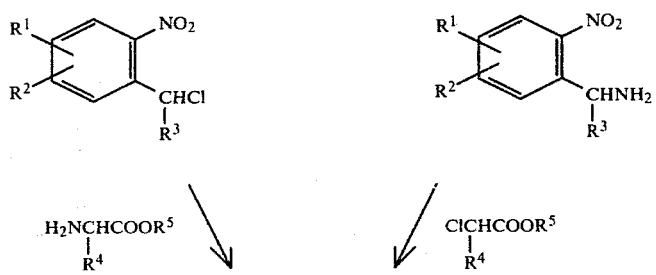

FORMULA SCHEME III

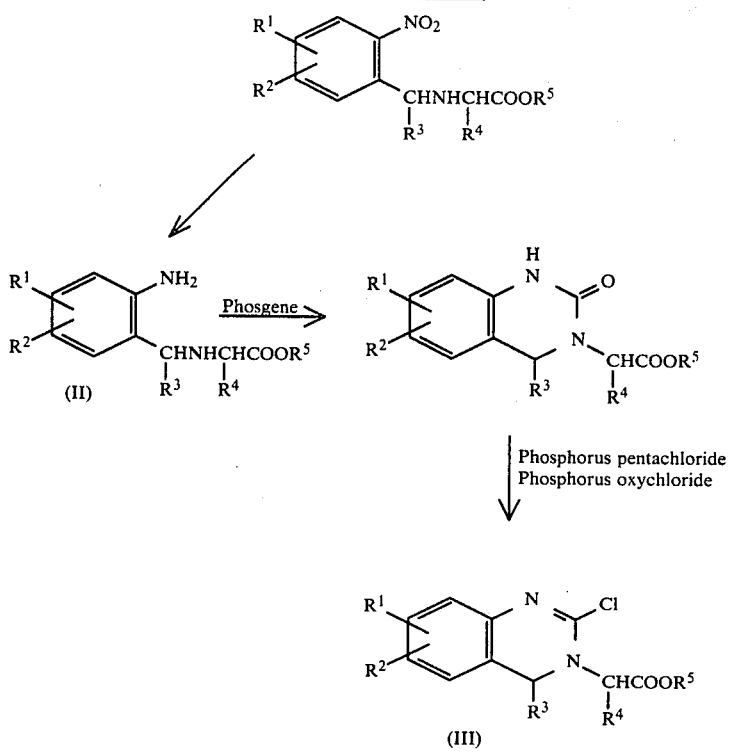

The compounds of formula I, their tautomers and the physiologically compatible salts or pharmaceutically acceptable acid addition salts of such compounds inhibit, for example, the aggregation of blood platelets and can therefore be used for the prophylaxis of thromboses. Moreover, the compounds of formula I, their tautomers and physiologically compatible salts or pharmaceutically acceptable acid addition salts of such compounds are active on the circulatory system. Due to their positive inotropic activity without substantial tachycardia, they can also be used for the treatment and prophylaxis of cardiac insufficiency and cardiac failure.

The compounds of formula I, their tautomers and the physiologically compatible salts or pharmaceutically acceptable acid addition salts of such compounds can be used as medicaments. For example, they can be used in the form of pharmaceutical preparations which contain them in association with a compatible pharmaceutical carrier material. Such carrier material can be an organic or inorganic inert carrier material suitable for enteral, percutaneous or parenteral administration such as, for example, water, gelatin, gum arabic, lactose, starch, magnesium stearate, talc, vegetable oils, polyalkyleneglycols, petroleum jelly, and the like. The pharmaceutical preparations can be made up in solid form, for example, as tablets, dragees, suppositories or capsules, in a semi-solid form, for example, as salves, or in a liquid form, for example, as solutions, suspensions or emulsions. The pharmaceutical preparations may be sterilized and/or may contain adjuvants, such as preserving, stabilizing, wetting or emulsifying agents, salts for varying the osmotic pressure or buffers. The pharmaceutical preparations can also contain still other therapeutically valuable substances. The compounds provided by the invention are preferably administered orally. A daily dosage of 0.5 mg/kg. to 30 mg/kg. may be administered to warm-blooded animals orally and a daily dosage of 0.05 mg/kg. to 10 mg/kg. may be administered parenterally.

The aggregation-inhibiting activity was demonstrated according to the aggregometer method of BORN [Nature 194, 927 (1962)] and MICHAL and BORN [Nature 231, 220 (1971)]. The maximum aggregation velocity was taken as the test parameter and the effective concentration ($EC_{50}$) was ascertained from dosage-activity curves.

Human plasma was obtained by centifugation from venous blood treated with citrate (10.6 mM). 0.18 ml. of plasma was treated with 10 μl of an aqueous suspension of the test substance and the mixture was incubated at 37° C. for 10 minutes, whereupon the aggregation was initiated by the addition of 10 μl of collagen-fibril suspension.

Rabbit plasma was obtained by centrifugation from arterial blood treated with citrate (9 mM). 1 ml. of plasma was treated with 10 μl of test solution and the mixture was incubated at 37° C. for 1 minute, whereupon 8 μl of collagen-fibril suspension or 10 μl. of adenosine diphosphate (ADP) in $10^{-4}$ N sodium chloride solution were added. Plasma incubated with dimethylsulfoxide served as the control.

The results are given in Table I hereinafter.

The positive inotropic activity was measured after the oral administration of a test substance to conscious sheepdogs. For this purpose, the animals are provided with an implanted pressure-telemetry system, so that the pressure receiver is fixed in the left ventricle. The left ventricular pressure is sent from the animal via the implanted radio transmitter and received via a suitable antenna and receiver system, demodulated and amplified. By differentiation of the ascending side of the left ventricular pressure (LVP), the maximum pressure increase rate (dLVP/dt$_{max}$) which represents the contractility parameter is calculated. Simultaneously, the heart frequency is recorded via a cardiotachograph. Under the heading inotropy in Table II, the percentage variation (Δ%) of dLVP/dt$_{max}$ and the duration of activity in minutes (min) are indicated. Under the heading tachycardia in Table II, the percentage variations of the heart frequency (Δ%) after administration of the test substance and the duration of activity in minutes (min) are indicated. The results are given in Table II hereinafter.

TABLE I

Collagen- and ADP-induced blood platelet aggregation

| Test substance (imidazoquinazoline derivative) | Rabbit plasma Collagen EC 50 μM | Rabbit plasma ADP EC 50 μM | Human plasma Collagen EC 50 μM |
|---|---|---|---|
| D-1,5-Dihydro-3,9-dimethyl-imidazo[2,1-b]quinazolin-2(3H)-one hydrochloride | 3.0 | 32 | 26 |
| L-1,5-Dihydro-3,9-dimethyl-imidazo[2,1-b]quinazolin-2(3H)-one hydrochloride | 18 | 60 | 49 |
| D-1,5-Dihydro-3,7-dimethyl-imidazo[2,1-b]quinazolin-2(3H)-one hydrochloride | 3.1 | 19 | 3.4 |
| L-1,5-Dihydro-3,7-dimethyl-imidazo[2,1-b]quinazolin-2(3H)-one hydrochloride | 22 | 77 | 33 |
| D-1,5-Dihydro-3,6-dimethyl-imidazo[2,1-b]quinazolin-2(3H)-one hydrochloride | 0.19 | 2.2 | 2.3 |
| L-1,5-Dihydro-3,6-dimethyl-imidazo[2,1-b]quinazolin-2(3H)-one hydrochloride | 0.93 | 11 | 6.2 |
| L-1,5-Dihydro-3-hydroxymethyl-6-methyl-imidazo-[2,1-b]quinazolin-2(3H)-one hydrochloride | — | — | 14 |

TABLE II

| Test substance (imidazoquinazoline derivative) | Dosage mg/kg | Inotropy Δ % | Inotropy Min | Heart frequency Δ % | Heart frequency Min |
|---|---|---|---|---|---|
| D-6-Chloro-1,5-dihydro-3-methyl-imidazo[2,1-b]-quinazolin-2(3H)-one hydrochloride | 5 | 93 | 145 | 28 | 115 |
| D-1,5-Dihydro-3,6-dimethyl-imidazo[2,1-b]quinazolin-2(3H)-one hydrochloride | 10 | 82 | 440 | 63 | 480 |
| L-1,5-Dihydro-3,9-dimethyl-imidazo[2,1-b]quinazolin-2(3H)-one hydrochloride | 10 | 43 | 120 | 16 | 100 |

The Examples which follow further illustrate the invention. All temperatures are in Degrees Centigrade, unless otherwise mentioned.

EXAMPLE 1

A solution of 5.3 g of cyanogen bromide in 10 ml of ethanol was added at room temperature while stirring to a solution of 11.8 g of N-(2-amino-3-methylbenzyl)-L-alanine ethyl ester in 30 ml of ethanol. The mixture was heated to reflux for 1 hour and then evaporated to dryness under reduced pressure. The residue was treated with 100 ml of water and made alkaline by the addition of 3-N ammonium hydroxide while stirring. The mixture was then stirred for a further 30 minutes and extracted three times with 100 ml of methylene chloride each time. The organic extracts were washed twice with 150 ml of water each time, dried over sodium sulfate and evaporated. The residue was recrystallized from ethanol and yielded L-1,5-dihydro-3,9-dimethylimidazo[2,1-b]quinazolin-2(3H)-one of melting point 259°–261° C.; $[\alpha]_D = +15.5°$ (c=1% in methanol).

By recrystallization of the thus-obtained base from 1-N hydrochloric acid/acetonitrile (3:1), there was obtained the hydrochloride of melting point 272°–275° C. (decomposition).

The starting material was prepared as follows:

A solution of 120 ml of triethylamine in 200 ml of absolute ethanol was added dropwise over a period of 30 minutes to a solution of 91.8 g of L-alanine ethyl ester hydrochloride in 300 ml of absolute ethanol. The mixture was warmed to 60° C., a clear solution resulting. To this solution was added dropwise within 1 hour a solution of 55.5 g of 3-(chloromethyl)-2-nitrotoluene in 300 ml of absolute ethanol. Thereafter, the temperature was increased to 80° C. and the mixture was stirred at this temperature overnight. Thereafter, the mixture was evaporated to dryness under reduced pressure and the residue was dissolved in 600 ml of water. The solution was extracted three times with methylene chloride and the extracts were washed successively with water and with saturated sodium chloride solution, dried and evaporated. The thus-obtained crude product was purified by chromatography on silica gel using methylene chloride/5% methanol for the elution. There was obtained N-(3-methyl-2-nitrobenzyl)-L-alanine ethyl ester in the form of a yellow oil; $[\alpha]_D = -36°$ (c=1% in methanol).

A solution of 26.6 g of N-(3-methyl-2-nitrobenzyl)-L-alanine ethyl ester in 100 ml of absolute ethanol was hydrogenated in the presence of 2 g of 10% palladium/carbon. 6.7 liters of hydrogen were taken up in 5 hours. After completion of the hydrogenation, the catalyst was filtered off and the filtrate was evaporated to dryness. There was obtained N-(2-amino-3-methylbenzyl)-L-alanine ethyl ester in the form of a yellow oil; $[\alpha]_D = -52.6°$ (c=1% in methanol).

In an analogous manner, from 3-(chloromethyl)-2-nitrotoluene and D-alanine ethyl ester hydrochloride there was obtained N-3-(methyl-2-nitrobenzyl)-D-alanine ethyl ester in the form of a yellow oil; $[\alpha]_D = +31.4°$ (c=1% in methanol);

from α³-chloro-4-nitro-m-xylene and L-alanine ethyl ester hydrochloride there was obtained N-(5-methyl-2-nitrobenzyl)-L-alanine ethyl ester in the form of a red oil; $[\alpha]_D = -12.6°$ (c=1% in methanol);

from α³-chloro-4-nitro-m-xylene and D-alanine ethyl ester hydrochloride there was obtained N-(5-methyl-2-nitrobenzyl)-D-alanine ethyl ester in the form of a red oil; $[\alpha]_D = +11.4°$ (c=1% in methanol);

from α²-chloro-3-nitro-o-xylene and L-alanine ethyl ester hydrochloride there was obtained N-(2-methyl-6-nitrobenzyl)-L-alanine ethyl ester in the form of a red oil; $[\alpha]_D = +35.8°$ (c=1% in methanol);

from α²-chloro-3-nitro-o-xylene and D-alanine ethyl ester hydrochloride there was obtained N-(2-methyl-6-nitrobenzyl)-D-alanine ethyl ester in the form of a red oil; $[\alpha]_D = -34°$ (c=1% in methanol);

from α²-chloro-3-nitro-o-xylene and L-serine ethyl ester hydrochloride there was obtained N-(2-methyl-6-nitrobenzyl)-L-serine ethyl ester in the form of a red oil; $n_D^{24} = 1.5474$;

from α²-chloro-3-nitro-o-xylene and D-α-phenylglycine ethyl ester hydrochloride there was obtained N-(2- methyl-6-nitrobenzyl)-D-α-phenylglycine ethyl ester in the form of a red oil; $n_D^{24} = 1.5261$;

from 2-nitrobenzyl chloride and L-alanine ethyl ester hydrochloride there was obtained 2-nitrobenzyl-L-alanine ethyl ester in the form of a dark red oil; $[\alpha]_D = -5.4°$ (c=1% in ethanol);

from 2-nitrobenzyl chloride and D-alanine ethyl ester hydrochloride there was obtained (2-nitrobenzyl)-D-alanine ethyl ester in the form of a red oil; $[\alpha]_D = +5.4°$ (c=1% in ethanol);

from N-3-methyl-2-nitrobenzyl-D-alanine ethyl ester there was obtained N-(2-amino-3-methylbenzyl)-D-alanine ethyl ester in the form of a light yellow oil; $[\alpha]_D = +51°$ (c=1% in methanol);

from N-(5-methyl-2-nitrobenzyl)-L-alanine ethyl ester there was obtained N-(2-amino-5-methylbenzyl)-L-alanine ethyl ester; $[\alpha]_D = -45°$ (c=1% in methanol);

from N-(5-methyl-2-nitrobenzyl)-D-alanine ethyl ester there was obtained N-(2-amino-5-methylbenzyl)-D-alanine ethyl ester in the form of a red oil; $[\alpha]_D = +34.2°$ (c=1% in methanol);

from N-(2-methyl-6-nitrobenzyl)-L-alanine ethyl ester there was obtained N-(2-amino-6-methylbenzyl)-L-alanine ethyl ester in the form of a yellow oil; $[\alpha]_D = -34.7°$ (c=1% in methanol);

from N-(2-methyl-6-nitrobenzyl)-D-alanine ethyl ester there was obtained N-(2-amino-6-methylbenzyl)-D-alanine ethyl ester in the form of a reddish oil; $[\alpha]_D = +36.8°$ (c=1% in methanol);

from N-(2-methyl-6-nitrobenzyl)-L-serine ethyl ester there was obtained N-(2-amino-6-methylbenzyl)-L-serine ethyl ester in the form of a red oil; $n_D^{24} = 1.5468$;

from N-(2-methyl-6-nitrobenzyl)-D-α-phenylglycine ethyl ester there was obtained N-(2-amino-6-methylbenzyl)-D-α-phenylglycine ethyl ester in the form of a yellow oil; $n_D^{24} = 1.5665$;

from (2-nitrobenzyl)-L-alanine ethyl ester there was obtained 2-aminobenzyl-L-alanine ethyl ester in the form of a red oil; $[\alpha]_D = -55.1°$ (c=1% in ethanol); and from 2-nitrobenzyl-D-alanine ethyl ester there was obtained 2-aminobenzyl-D-alanine ethyl ester in the form of a dark red oil; $[\alpha]_D = +57.2°$ (c=1% in ethanol).

EXAMPLE 2

In a manner analogous to that described in Example 1, from N-(2-amino-3-methylbenzyl)-D-alanine ethyl ester, there was obtained D-1,5-dihydro-3,9-dimethylimidazo[2,1-b]-quinazolin-2(3H)-one hydrochloride of melting point 270°-275° C. (decomposition). The free base melts at 262°-265° C.

EXAMPLE 3

In a manner analogous to that described in Example 1, from N-(2-amino-5-methylbenzyl)-L-alanine ethyl ester, there was obtained L-1,5-dihydro-2,7-dimethylimidazo[2,1-b]-quinazolin-2(3H)-one hydrochloride in the form of light yellow crystals of melting point 173°-176° C. The free base melts above 300° C. with decomposition.

EXAMPLE 4

In a manner analogous to that described in Example 1, from N-(2-amino-5-methylbenzyl)-D-alanine ethyl ester there was obtained D-1,5-dihydro-3,7-dimethylimidazo[2,1-b]-quinazolin-2(3H)-one hydrochloride in the form of light yellow crystals of melting point 173°-176° C. (decomposition). The free base melts at 310°-314° C. with decomposition.

EXAMPLE 5

In a manner analogous to that described in Example 1, from N-(2-amino-6-methylbenzyl)-L-alanine ethyl ester there was obtained L-1,5-dihydro-3,6-dimethylimidazo[2,1-b]-quinazoline-2(3H)-one hydrochloride in the form of colorless crystals of melting point 285°-288° C. (decomposition). The free base melts above 340° C. with decomposition.

EXAMPLE 6

In a manner analogous to that described in Example 1, from N-(2-amino-6-methylbenzyl)-D-alanine ethyl ester there was obtained D-1,5-dihydro-3,6-dimethylimidazo[2,1-b]-quinazolin-2(3H)-one hydrochloride in the form of light yellow crystals of melting point 287°-290° C. (decomposition). The free base melts above 340° C.

EXAMPLE 7

In a manner analogous to that described in Example 1, from N-(2-amino-6-methylbenzyl)-L-serine ethyl ester there was obtained L-1,5-dihydro-3-hydroxymethyl-6-methyl-imidazo[2,1-b]quinazoline-2(3H)-one hydrochloride in the form of yellow crystals of melting point 320°-325° C. (decomposition).

EXAMPLE 8

In a manner analogous to that described in Example 1, from N-(2-amino-6-methylbenzyl)-D-α-phenylglycine ethyl ester there was obtained D-1,5-dihydro-3-phenyl-6-methyl-imidazo[2,1-b]quinazolin-2(3H)-one hydrochloride in the form of light yellow crystals of melting point about 320° C. (decomposition).

EXAMPLE 9

In a manner analogous to that described in Example 1, from 2-amino-benzyl-L-alanine ethyl ester there was obtained L-1,5-dihydro-3-methyl-imidazo[2,1-b]quinazolin-2(3H)-one hydrochloride in the form of brown crystals of melting point 223°-226° C. The free base melts at 300°-305° C. with decomposition.

EXAMPLE 10

In a manner analogous to that described in Example 1, from 2-amino-benzyl-D-alanine ethyl ester there was obtained D-1,5-dihydro-3-methyl-imidazo[2,1-b]quinazolin-2(3H)-one hydrochloride in the form of yellow crystals of melting point 225°-227° C. The free base melts at about 300° C. with decomposition.

EXAMPLE 11

A solution of 5 g of cyanogen bromide in 20 ml of ethanol was added dropwise at room temperature while stirring to a solution of 11.9 g of N-(2-amino-6-chlorobenzyl)-L-alanine ethyl ester in 20 ml of ethanol. The mixture was then boiled at reflux for 1 hour and evaporated to dryness. The residue was treated with 150 ml of water and made alkaline with 3-N ammonium hydroxide while stirring. After stirring for 30 minutes, the precipitate was filtered off and recrystallised from 1-N hydrochloric acid and acetonitrile. There were obtained 9.1 g (68% of theory) of L-6-chloro-1,5-dihydro-3-methyl-imidazo[2,1b]-quinazolin-2(3H)-one hydrochloride in the form of yellow crystals of melting point 260°–263° C.; $[\alpha]_D = +34.2°$ (in dimethylsulfoxide).

In an analogous manner, from N-(2-amino-6-chlorobenzyl)-D-alanine ethyl ester there was obtained D-6-chloro-1,5-dihydro-3-methyl-imidazo[2,1-b]quinazolin-2(3H)-one hydrochloride of melting point 263°–266° C.; $[\alpha]_D = -23.9°$ (in dimethylsulfoxide); melting point of the free base 275°–280° C.

The starting material can be prepared as follows:

18.24 g of L-alanine ethyl ester hydrochloride in 60 ml of ethanol was added dropwise to a mixture of 25 ml of triethylamine in 60 ml of ethanol and the mixture was heated to 80° C. The resulting solution was added dropwise at this temperature to a solution of 15 g of α-bromo-2-chloro-6-nitrotoluene in 60 ml of ethanol. The mixture was stirred at 80° C. overnight and then evaporated to dryness. The residue was treated with 150 ml of deionised water and extracted twice with 100 ml of methylene chloride. The methylene chloride extracts were washed with water, dried and evaporated. The resulting product was purified by chromatography on silica gel with methylene chloride/5% methanol. There were obtained 15.75 g (91% of theory) of N-(2-chloro-6-nitrobenzyl)-L-alanine ethyl ester; $n_D^{20} = 1.5267$.

N-(2-Chloro-6-nitrobenzyl)-D-alanine ethyl ester ($n_D^{25} = 1.5247$) was obtained in an analogous manner from D-alanine ethyl ester and α-bromo-2-chloro-6-nitrotoluene.

A solution of 14.3 g of N-(2-chloro-6-nitrobenzyl)-L-alanine ethyl ester in 50 ml of absolute ethanol was hydrogenated in the presence of 1 g of Raney nickel. After completion of the hydrogenation, the catalyst was filtered off and the filtrate was evaporated to dryness. There were obtained 12.6 g (99% of theory) of N-(2-amino-6-chlorobenzyl)-L-alanine ethyl ester; $n_D^{22} = 1.5430$.

N-(2-Amino-6-chlorobenzyl)-D-alanine ethyl ester ($n_D^{23} = 1.5405$) was obtained in an analogous manner by hydrogenating N-(2-chloro-6-nitrobenzyl)-D-analine ethyl ester.

EXAMPLE 12

In a manner analogous to that described in Example 11 there were obtained:

D-6,7-Dichloro-1,5-dihydro-3-methyl-imidazo[2,1-b]-quinazolin-2(3H)-one hydrochloride of melting point above 280° C., L-6,7-dichloro-1,5-dihydro-3-methyl-imidazo[2,1-b]-quinazolin-2(3H)-one hydrochloride of melting point above 290° C., D-7-bromo-1,5-dihydro-3-methyl-imidazo[2,1-b]-quinazolin-2(3H)-one hydrochloride of melting point 268°–270° C.

L-7-bromo-1,5-dihydro-3-methyl-imidazo[2,1-b]quinazolin-2(3H)-one hydrochloride of melting point 280°–284° C. (decomposition), and L-6-chloro-1,5-dihydro-3-methyl-7-methoxy-imidazo[2,1-b]quinazolin-2(3H)-one hydrochloride of melting point above 280° C.

EXAMPLE 13

In a manner analogous to that described in Example 11, from N-(2-chloro-6-nitrobenzyl)-3-phenyl-D-alanine ethyl ester $[[\alpha]_D = -21.2°$ (c=1% in ethanol)] there was obtained, via N-(2-amino-6-chlorobenzyl)-3-phenyl-D-alanine ethyl ester $[[\alpha]_D = +40.7°$ (c=1% in ethanol)], D-3-benzyl-6-chloro-1,5-dihydro-imidazo[2,1-b]quinazolin-2(3H)-one hydrochloride of melting point 260°–265° C. (decomposition); melting point of the base 270°–275° C. (decomposition);

from N-(2-chloro-6-nitrobenzyl)-D-leucine ethyl ester there was obtained, via N-(2-amino-6-chlorobenzyl)-D-leucine ethyl ester $[[\alpha]_D = +8.5°$ (c=1% in ethanol)], D-6-chloro-1,5-dihydro-3-isobutyl-imidazo[2,1-b]quinazolin-2(3H)-one hydrochloride of melting point 290°–293° C.; melting point of the base 280°–285° C.;

from N-(2-chloro-6-nitrobenzyl)-D-serine ethyl ester $[[\alpha]_D = 2.7°$ (c=1% in ethanol)] there was obtained, via N-(2-amino-6-chlorobenzyl)-D-serine ethyl ester [melting point 73°–75° C.; $[\alpha]_D = +65.5°$ (c=1% in ethanol)], D-6-chloro-3-hydroxymethyl-1,5-dihydro-imidazo[2,1-b]quinazolin-2(3H)-one hydrochloride; melting point of the base above 300° C. (decomposition); and from D-N-(2-chloro-6-nitrobenzyl)-2-phenylglycine ethyl ester $[[\alpha]_D = -21°$ (c=1% in ethanol)] there was obtained, via D-N-(2-amino-6-chlorobenzyl)-2-phenylglycine ethyl ester $[[\alpha]_D = -4.5°$ (c=1% in ethanol)], D-6-chloro-3-phenyl-1,5-dihydro-imidazo[2,1-b]quinazolin-2(3H)-one hydrochloride of melting point above 300° C. (decomposition); melting point of the base 260°–265° C. (decomposition).

EXAMPLE 14

A mixture of 6 g of ethyl D-2,5-dichloro-α-methyl-3(4H)-quinazolinacetate, 20 ml of absolute ethanol and 25 ml of 5% alcoholic ammonia was heated to 110° C. overnight in a pressure tube. The pressure tube was cooled in an ice-bath and opened. The resulting crystal slurry was filtered off under suction and washed with cold ethanol. The crystals obtained were dissolved in 1-N hydrochloric acid and filtered. The filtrate was evaporated to dryness and the residue was recrystallized from 1-N hydrochloric acid and acetonitrile to give 4.3 g (74% of theory) of D-6-chloro-1,5-dihydro-3-methyl-imidazo[2,1-b]quinazolin-2(3H)-one hydrochloride of melting point 275°–278° C.

The starting material can be prepared as follows:

A mixture of 18.24 g of D-alanine ethyl ester hydrochloride in 60 ml of ethanol was added dropwise to a mixture of 25 ml of triethylamine in 60 ml of ethanol and the resulting mixture was heated to 80° C. The solution obtained was added dropwise at this temperature to a solution of 15 g of 2-chloro-6-nitrobenzyl bromide in 60 ml of ethanol. The mixture was stirred at 80° C. overnight and then evaporated to dryness. The residue was treated with 150 ml of deionised water and extracted twice with 100 ml of methylene chloride. The methylene chloride extracts were washed with water, dried over sodium sulphate and evaporated. The resulting product was purified by chromatography on silica gel with methylene chloride/5% methanol. There were obtained 16 g (93% of theory) of N-(2-chloro-6-nitrobenzyl)-D-alanine ethyl ester; $n_D^{25} = 1.5247$; $[\alpha]_D = -6.9°$ (c=1% in ethanol).

A solution of 14.3 g of N-(2-chloro-6-nitrobenzyl)-D-alanine ethyl ester in 50 ml of ethanol was hydrogenated in the presence of 1 g of Raney nickel. 3.35 liters of hydrogen were taken up in 2 hours. The catalyst was then filtered off and the filtrate was evaporated to dryness. There were obtained 12.6 g (99% of theory) of N-(2-amino-6-chlorobenzyl)-D-alanine ethyl ester; $n_D^{23} = 1.5405$; $[\alpha]_D = +55.8°$ (c=1% in ethanol).

52 g of N,N'-carbonyldiimidazole were added portionwise while gassing with nitrogen and stirring to a solution of 71.75 g of N-(2-amino-6-chlorobenzyl)-D- alanine ethyl ester in 400 ml of dry tetrahydrofuran. The mixture was stirred for 2 hours, heated under reflux for 18 hours and evaporated to dryness. The residue was extracted with 1500 ml of methylene chloride, the organic phase was washed twice with 400 ml of 1-N hydrochloric acid and then with 400 ml of water, dried and evaporated. The resulting oil was purified by chromatography on silica gel with methylene chloride/5% methanol. There were obtained 79 g (99% of theory) of ethyl D-5-chloro-1,4-dihydro-α-methyl-2-oxo-3(2H)-quinazolinacetate; $[\alpha]_D^{25} = -40.8°$ (c=1% in ethanol).

50.9 g of ethyl D-5-chloro-1,4-dihydro-α-methyl-2-oxo-3(2H)-quinazolinacetate were dissolved in 135 ml of phosphorus oxychloride and heated to 110° C. for 3 hours while stirring. After cooling, the mixture was evaporated to dryness, the residue was dissolved in 250 ml of chloroform, the solution was diluted with 300 ml of ice/water and adjusted to pH 7–8 by the dropwise addition of 40% sodium hydroxide. The chloroform phase was separated, dried and evaporated. The product was purified by chromatography on silica gel with methylene chloride/5% methanol. There were obtained 37.4 g (70% of theory) of ethyl D-2,5-dichloro-α-methyl-3(4H)-quinazolinacetate; $n_D^{22} = 1.5775$.

EXAMPLE 15

1.5 ml of bromine were added dropwise to a solution of 5 g of D-1,5-dihydro-3-methyl-imidazo[2,1-b]quinazolin-2(3H)-one in 80 ml of glacial acetic acid. The mixture was stirred at room temperature for 1.5 hours, diluted with 100 ml of water, concentrated to 30 ml, again diluted with 100 ml of water, made alkaline with 3-N ammonium hydroxide, washed and filtered. The separated product was washed with water and recrystallised from 100 ml of 2-N hydrochloric acid. There were obtained 3.9 g (56% of theory) of D-7-bromo-1,5-dihydro-3-methyl-imidazo[2,1-b]quinazolin-2(3H)-one hydrochloride of melting point 268°–270° C.

EXAMPLE 16

In a manner analogous to that described in Example 15, 4.7 g of L-1,5-dihydro-3-methyl-imidazo[2,1-b]quinazolin-2(3H)-one were brominated to give 4.2 g (64% of theory) of L-7-bromo-1,5-dihydro-3-methyl-imidazo[2,1-b]quinazolin-2(3H)-one hydrochloride of melting point 280°–284° C. (decomposition).

The following Examples illustrate pharmaceutical preparations containing the imidazoquinazoline derivatives provided by the present invention:

EXAMPLE 17

302 G. of 3-nitro-o-xylene in 2000 ml. of carbon tetrachloride are added to 391 g. of N-bromosuccinimide and 10 g. of dibenzoylperoxide in 1000 ml. of carbon tetrachloride. The mixture is heated to reflux for 3–4 hours, then cooled to room temperature and filtered. The filtrate is evaporated to dryness, yielding 480 g. of a mixture of the isomers, 2-methyl-6-nitrobenzylbromide and 2-methyl-3-nitrobenzylbromide.

900 Ml. of triethylamine in 1000 ml. of ethanol are added dropwise to 380 g. of D-alanine ethyl ester hydrochloride in 1500 ml. of ethanol. The mixture is warmed to 70° C., and treated with the above-mentioned 480 g. of bromides in 1000 ml. of ethanol. The mixture is heated to reflux for 3–4 hours, evaporated to dryness, treated with 1500 ml. of water and extracted with methylene chloride. The extracts are washed with water, dried and evaporated, yielding 534 g. of a mixture of the isomers, N-(2-methyl-6-nitrobenzyl)-D-alanine ethyl ester and N-(2-methyl-3-nitrobenzyl)-D-alanine ethyl ester.

This mixture in 1000 ml. of ethanol is hydrogenated over 50 g. of 10% palladium/carbon. After the catalyst is filtered off, 186 g. of cyanogen bromide are added to the filtrate. The mixture is stirred for 48 hours, then made alkaline by 300 ml. of concentrated ammonium hydroxide and stirred for 1–2 hours, precipitate filtered, washed with water and dried, yielding 54.4 g. of D-1,5-dihydro-3,6-dimethylimidazo[2,1-b]quinazolin-2(3H)-one.

52 G. of bromine in 200 ml. of glacial acetic acid are added to 64 g. of D-1,5-dihydro-3,6-dimethylimidazo[2,1-b]quinazolin-2(3H)-one in 400 ml. of glacial acetic acid. After 2 hours, the reaction mixture is filtered and the precipitate (97.4 g., m.p. 250°–255° C.) is washed with glacial acetic acid, dried and recrystallized from methanol diethylether to yield 64.8 g. of D-7-bromo-1,5-dihydro-3,6-dimethyl-imidazo[2,1-b]quinazolin-2(3H)-one hydrobromide, m.p. 277°–279° C. (decomposition) corresponding base, m.p. above 300° C., D-7-bromo-1,5-dihydro-3,6-dimethyl-imidazo[2,1-b]quinazolin-2(3H)-one.

EXAMPLE 18

In analogy to the procedure of Example 17, for the preparation of D-1,5-dihydro-3,6-dimethyl-imidazo[2,1-b]quinazolin-2(3H)-one, starting from 3-nitro-o-xylene, there are obtained:

D-6-chloro-1,5-dihydro-3-methyl-imidazo[2,1-b]quinazolin-2(3H)-one;

D-6-bromo-1,5-dihydro-3-methylimidazo[2,1-b]quinazolin-2(3H)-one;

D-6-chloro-7-methoxy-1,5-dihydro-3-methyl-imidazo[2,1-b]quinazolin-2(3H)-one;

D-6,7-dichloro-1,5-dihydro-3-methyl-imidazo[2,1-b]quinazolin-2(3H)-one; and

D-6-chloro-7-bromo-1,5-dihydro-3-methyl-imidazo[2,1-b]quinazolin-2(3H)-one.

Starting materials are 1-chloro-2-methyl-3-nitrobenzene, 1-bromo-2-methyl-3-nitrobenzene, 1-chloro-6-methoxy-2-methyl-3-nitrobenzene, 1,6-dichloro-2-methyl-3-nitrobenzene and 1-bromo-2-chloro-3-methyl-4-nitrobenzene, respectively.

EXAMPLE A

Tablets containing the following ingredients were manufactured in the usual manner:

| | |
|---|---|
| D-6-Chloro-1,5-dihydro-3-methyl-imidazo[2,1-b]quinazolin-2(3H)-one hydrochloride | 184.6 mg |
| Lactose | 15.0 mg |
| Maize starch | 37.9 mg |
| Water-soluble polyvinylpyrrolidone | 10.0 mg |
| Magnesium stearate | 2.5 mg |
| Total weight per tablet | 250.0 mg |

EXAMPLE B

Interlocking gelatin capsules containing the following ingredients were manufactured in the usual manner:

D-6-Chloro-1,5-dihydro-3-methyl-imidazo[2,1-b]quinazolin-2(3H)-

-continued

| | |
|---|---|
| one hydrochloride | 200.0 mg |
| Water-soluble polyvinylpyrrolidone | 2.0 mg |
| Maize starch | 43.0 mg |
| Talc | 4.5 mg |
| Magnesium stearate | 0.5 mg |
| Total weight per capsule | 250.0 mg |

EXAMPLE C

An injection solution containing the following ingredients was manufactured in the usual manner:

| | |
|---|---|
| D-6-Chloro-1,5-dihydro-3-methyl-imidazo[2,1-b]quinazolin-2 (3H)-one hydrochloride | 114.16 mg |
| Glycerinformal | 2.4 ml |
| Water | 4.0 ml |

I claim:
1. A compound of the group consisting of
D-6-chloro-1,5-dihydro-3-methyl-imidazo[2,1-b]quinazolin-2(3H)-one;
D-7-bromo-1,5-dihydro-3,6-dimethyl-imidazo[2,1-b]quinazolin-2(3H)-one;
D-6-chloro-1,5-dihydro-7-methoxy-3-methyl-imidazo[2,1-b]quinazolin-2-(3H)-one;
D-6,7-dichloro-1,5-dihydro-3-methyl-imidazo[2,1-b]quinazolin-2(3H)-one;
D-7-bromo-6-chloro-1,5-dihydro-3-methyl-imidazo[2,1-b]quinazolin-2(3H)-one;
D-3,6-dimethyl-1,5-dihydro-imidazo[2,1-b]quinazolin-2-(3H)-one;
L-3,6-dimethyl-1,5-dihydro-imidazo[2,1-b]quinazolin-2(3H)-one;
L-3,9-dimethyl-1,5-dihydro-imidazo[2,1-b]quinazolin-2(3H)-one;
D-7-bromo-1,5-dihydro-3-methyl-imidazo[2,1-b]quinazoline-2(3H)-one,
their tautomers and pharmaceutically acceptable acid addition salts.

2. A compound in accordance with claim 1, D-6-chloro-1,5-dihydro-3-methyl-imidazo[2,1-b]quinazolin-2(3H)-one or a pharmaceutically acceptable acid addition salt thereof.

3. A compound in accordance with claim 1, L-1,5-dihydro-3,9-dimethylimidazo-[2,1-b]quinazolin-2(3H)-one or a pharmaceutically acceptable salt thereof.

4. A compound in accordance with claim 1, D-1,5-dihydro-3,6-dimethyl-imidazo[2,1-b]quinazolin-2(3H)-one or a pharmaceutically acceptable salt thereof.

5. A compound in accordance with claim 1, L-1,5-dihydro-3,6-dimethyl-imidazo[2,1-b]quinazolin-2(3H)-one or a pharmaceutically acceptable salt thereof.

6. A compound in accordance with claim 1, D-6-chloro-1,5-dihydro-3-methyl-7-methoxy-imidazo[2,1-b]quinazolin-2(3H)-one or a pharmaceutically acceptable salt thereof.

7. A compound in accordance with claim 1, D-7-bromo-6-chloro-1,5-dihydro-3-methyl-imidazo[2,1-b]quinazolin-2(3H)-one or a pharmaceutically acceptable salt thereof.

8. A compound in accordance with claim 1, D-7-bromo-1,5-dihydro-3-methyl-imidazo[,1-b]quinazolin-2(3H)-one or a pharmaceutically acceptable salt thereof.

9. A compound in accordance with claim 1, D-6,7-dichloro-1,5-dihydro-3-methyl-imidazo[2,1-b]quinazolin-2(3H)-one or a pharmaceutically acceptable salt thereof.

10. A compound in accordance with claim 1, D-7-bromo-1,5-dihydro-3,6-dimethyl-imidazo[2,1-b]quinazolin-2(3H)-one or a pharmaceutically acceptable salt thereof.

11. A pharmaceutical composition for the treatment and prophylaxis of cardiac insufficiency and cardiac failure containing an effective amount for such treatment and prophylaxis of a compound of the group consisting of
D-6-chloro-1,5-dihydro-3-methyl-imidazo[2,1-b]quinazolin-2(3H)-one;
D-7-bromo-1,5-dihydro-3,6-dimethyl-imidazo[2,1-b]quinazolin-2(3H)-one;
D-6-chloro-1,5-dihydro-7-methoxy-3-methyl-imidazo[2,1-b]quinazolin-2-(3H)-one;
D-6,7-dichloro-1,5-dihydro-3-methyl-imidazo[2,1-b]quinazolin-2(3H)-one;
D-7-bromo-6-chloro-1,5-dihydro-3-methyl-imidazo[2,1-b]quinazolin-2(3H)-one;
D-3,6-dimethyl-1,5-dihydro-imidazo[2,1-b]quinazolin-2(3H)-one;
L-3,6-dimethyl-1,5-dihydro-imidazo[2,1-b]quinazolin-2(3H)-one;
L-3,9-dimethyl-1,5-dihydro-imidazo[2,1-b]quinazolin-2(3H)-one;
D-7-bromo-1,5-dihydro-3-methyl-imidazo[2,1-b]quinazoline-2(3H)-one,
their tautomers and pharmaceutically acceptable acid addition salts in association with a compatible pharmaceutical carrier material.

* * * * *